(12) United States Patent
Gu et al.

(10) Patent No.: US 6,200,751 B1
(45) Date of Patent: Mar. 13, 2001

(54) ENDOTHELIAL SPECIFIC EXPRESSION REGULATED BY EPCR CONTROL ELEMENTS

(75) Inventors: Jian-Ming Gu; Charles T. Esmon, both of Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 08/965,729

(22) Filed: Nov. 7, 1997

Related U.S. Application Data (60) Provisional application No. 60/030,718, filed on Nov. 8, 1996, and provisional application No. 60/054,533, filed on Aug. 4, 1997.

(51) Int. Cl.[7] .............................. C12Q 1/68; C07H 21/04
(52) U.S. Cl. .............................................. 435/6; 536/24.1
(58) Field of Search .................................. 435/6; 514/44; 536/24.1

(56) References Cited

U.S. PATENT DOCUMENTS

| | | | |
|---|---|---|---|
| 3,625,214 | 12/1971 | Higuchi | 424/424 |
| 4,244,946 | 1/1981 | Rivier et al. | 514/15 |
| 4,305,872 | 12/1981 | Johnston et al. | 530/33 |
| 4,316,891 | 2/1982 | Guillemin et al. | 514/11 |
| 4,629,784 | 12/1986 | Stammer | 530/328 |

(List continued on next page.)

FOREIGN PATENT DOCUMENTS

| | | |
|---|---|---|
| WO 93/09236 A1 | 5/1993 | (WO) . |
| WO 94/04694 A1 | 3/1994 | (WO) . |
| WO 96/05303 A1 | 2/1996 | (WO) . |

OTHER PUBLICATIONS

Agrawal, et al., "Oligodeoxynucleoside phosphoramidates and phosphorothioates as inhibitors of human immunodeficiency virus," *Proc. Natl. Acad. Sci. USA* 85:7079–7083 (1988).
Askew, et al., "Molecular Recognition with Convergent Functional Groups, 6. Synthetic and Structural Studies with a Model Receptor for Nucleic Acid Components," *J. Am. Chem. Soc.* 111:1082–1090 (1989).
Bangalore, et al., "High Affinity Binding Sites for Activated Protein C and Protein C on Cultured Human Umbilical Vein Endothelial Cells," *Thrombosis and Haemostasis* 72(3):465–474 (1994).
Blume, et al., "Triple helix formation by purine–rich oligonucleotides targeted to the human dihydrofolate reductase promoter," *Nucl. Acids Res.* 20(7):1777–1784 (1992).
Bock, "Active Site Selective Labeling of Serina Proteases with Spectroscopic Probes Using Thioester Peptide Chloromethyl Ketones Demonstration of Thrombin Labeling Using $N^{\alpha}$– [(Acetylthio)acetyl]–D–Phe–Pro–Arg–$CH_2Cl$," *Biochemistry* 27:6633–6639 (1988).
Clackson, et al., "Making antibody fragments using phage display libraries," *Nature* 352:624–688 (1991).
Conway, et al., "Tumor Necrosis Factor Suppresses Transcription of the Thrombomodulin Gene in Endothelial Cells," *Mol. Cell. Biol.* 8(12):5588–5592 (1988).
Cooney, et al., "Site–Specific Oligonucleotide Binding Represses Transcription of the Human c–myc Gene In Vitro," *Science* 241:456–459 (1988).
Crooke, "Progress toward oligonucleotide therapeutics: pharmacodynamic properties," *FASEB J.* 7:533–539 (1993).
Dahlbäck, "Protein S and C4b–Binding Protein: Components Involved in the Regulation of the Protein C Anticoagulant System," *Thromb. Haemostas.* 66(1):49–61 (1991).
Dahlbäck, "Inhibition of Protein $C_a$, Cofactor Function of Human and Bovine Protein S by C4b–binding Protein," *J. Biol. Chem.* 261(26):12022–12027 (1986).
Dahlbäck, "Binding of Anticoagulant Vitamin K–Dependent Protein S to Platelet–Derived Microparticles," *Biochemistry* 31:12769–12777 (1992).
Daugherty, et al., "Polymerase chain reaction facilitates the cloning, CDR–grafting, and rapid expression of a murine monoclonal antibody directed against the CD18 component of leukocyte integrins," *Nucl. Acids Res.* 19(9):2471–2476 (1991).

(List continued on next page.)

*Primary Examiner*—George C. Elliott
*Assistant Examiner*—William Sandals
(74) *Attorney, Agent, or Firm*—Arnall Golden & Gregory, LLP (57) ABSTRACT

The promoter of the EPCR gene has been isolated from both murine (SEQ. ID No. 1) and human (SEQ. ID No. 2) genomic libraries. The promoter includes a region (nucleotides 3130 to 3350 of SEQ. ID No. 1 which affects selective gene expression in endothelial cells), and a region (nucleotides 2270 to 2840 of SEQ. ID No. 1) which affects selective gene expression in large vessel endothelial cells, as compared to expression in all endothelial cells. The EPCR promoter contains a thrombin responsive element, CCCAC-CCC (SEQ. ID No. 3), (murine, nucleotides 3007 to 3014 SEQ. ID No. 1 and human, nucleotides 2722 to 2729 SEQ. ID No. 2). The EPCR also contains a serum response element (nucleotides 2990 to 3061 of SEQ. ID No. 1). The regulatory sequences present in the EPCR promoter can be used for thrombin or serum controlled recombinant gene expression specific to either all endothelial cells or primarily endothelial cells of large vessels. Therapeutic strategies include the use of the minimal promoter for expression of therapeutic agents during times of increased thrombin/platelet activation or regional trauma in all endothelial cells or the use of the large vessel specific promoter for regional specific expression in the endothelial cells of large vessels for use in delivery.

22 Claims, 5 Drawing Sheets

U.S. PATENT DOCUMENTS

| | | | |
|---|---|---|---|
| 4,789,734 | 12/1988 | Pierschbacher | 530/395 |
| 4,792,525 | 12/1988 | Ruoslahti et al. | 435/402 |
| 4,868,116 | 9/1989 | Morgan et al. | 435/456 |
| 4,906,474 | 3/1990 | Langer et al. | 514/772.3 |
| 4,925,673 | 5/1990 | Steiner et al. | 424/455 |
| 4,980,286 | 12/1990 | Morgan et al. | 435/69.1 |
| 5,009,889 | 4/1991 | Taylor et al. | 424/94.64 |

OTHER PUBLICATIONS

Dittman, et al., "Structure and Function of Thrombomodulin: A Natural Anticoagulant," *Blood* 75(2):329–336 (1990).

Dittman, "Thrombodulin—Biology and Potential Cardiovascular Applications," *Trends Cardiovasc. Med.* 1(8):331–336 (1991).

Dreyfus, et al., "Treatment of Homozygous Protein C Deficiency and Neonatal Purpura Fulminans With a Purified Protein C Concentrate," *N. Engl. J. Med.* 325(22):1565–1568 (1991).

Duval–Valentin, et al., "Specific inhibition of transcription by triple helix–forming oligonucleotides," *Proc. Natl. Acad. Sci. USA* 89:504–508 (1992).

Ecke, et al., "Possible identity of kallikrein binding protein with protein C inhibitor," *Agents and Actions* (Supp.) vol. 38, pp. 182–189 (Abstract only).

Engelman, et al., "Identifying Nonpolar Transibilayer Helices in Amino Acid Sequences of Membrane Proteins," *Annu. Rev. Biophys. Biophys. Chem.* 15:321–353 (1986).

Esmon, "The Roles of Protein C and Thrombomodulin in the Regulation of Blood Coagulation," *J. Biol. Chem.* 264(9):4743–4746 (1989).

Esmon, "Protein S and Protein C—Biochemistry, Physiology, and Clinical Manifestation of Deficiencies," *Trends Cardiovasc. Med.* 2(6):214–220 (1992).

Esmon, et al., "Protein C Activation," *Meths. Enzymol.* 222:359–385 (1993).

Fukudome, et al., "Molecular Cloning and Expression of Murine and Bovine Endothelial Cell Protein C/Activated Protein C Receptor (EPCR)," *J. Biological Chemistry* 270(10):5571–5577 (1995).

Fukudome, et al., "Identification, Cloning, and Regulation of Novel Endothelial Cell Protein C/activated Protein C Receptor," *Circulation* 90(4) part 2; Abstract No. 0707 (1994).

Fukudome, et al., "Identification, Cloning, and Regulation of Novel Endothelial Cell Protein C/Activated Protein C Receptor," *J. Biol. Chem.* 269(42):26486–26491 (1994).

Fukudome, et al., "The Endothelial Cell Protein C Receptor," *J. Biol. Chem.* 271(29):17491–17498 (1996).

Gardner, et al., "Mouse Lymphotoxin and Tumor Necrosis Factor: Structural Analysis of the Cloned Genes, Physical Linkage, and Chromosomal Position," *J. Immunol.* 139(2):476–483 (1987).

Gerson, et al., "Severe Acquired Protein C Deficiency in Purpura Fulminans Associated with Disseminated Intravascular Coagulation: Treatment with Protein C Concentrate," *Pediatrics* 91(2):418–422 (1993).

Graham, et al., "A New Technique for the Assay of Infectivity of Human Adenovirus 5 DNA," *Virology* 52:456–467 (1973).

Gregoriadis, "Liposomes," *Drug Carriers in Biology and Medicine*, Chap. 14, pp. 287–341 (Academic Press, 1979).

Grey, et al., "Selective Effects of Protein C on Activation of Human Monocytes by Lipopolysaccharide, Interferon–Y, or PMA: Modulation of Effects on CD11b and CD14 but not CD25 or CD54 Induction," *Transplant Proc.* 25(5):2913–2914 (1993).

Grigoriev, et al., "A Triple Helix–forming Oligonucleotide–Intercalator Conjugate Acts as a Transcriptional Repressor via Inhibition of NF kB Binding to Interleukin–2 Receptor α–Regulatory Sequence," *J. Biol. Chem.* 267:3389–3395 (1992).

Grinnell, et al., "Human Protein C inhibits selectin–mediated cell adhesion: role of unique fucosylated oligosaccharide," *Glycobiology* 4(2):221–226 (1994).

Gu, et al., "Functional Characterization of 5'–Flanking Region of the Mouse Endothelial Protein C Receptor (EPCR) Gene," *Mol. Biol. Cell* Supp. 8:228a, Abstract No. 1323 (1997).

Hogg, et al., "Identification of Structural Domains in Protein C Involved in Its Interaction with Thrombin–Thrombomodulin on the Surface of Endothelial Cells," *J. Biol. Chem.* 267:703–706 (1992).

Holt, et al., "An Oligomer Complementary to c–myc mRNA Inhibits Proliferation of HL–60 Promyelocytic Cells and Induces Differentiation," *Mol. Cell. Biol.* 8(2):963–973 (1988).

Itakura, et al., "Synthesis and Use of Synthetic Oligonucleotides," *Ann. Rev. Biochem.* 53:323–356 (1984).

Kaisho, et al., "BST–1, a surface molecule of bone marrow stromal cell lines that facilitates pre–B–cell growth," *Proc. Natl. Acad. Sci. (USA)* 91:5325–5329 (1994).

Kapiotis, et al., "Interleukin–4 Counteracts Pyrogen–Induced Downregulation of Thrombomodulin in Cultured Human Vascular Endothelial Cells," *Blood* 78(2):410–415 (1991).

Kozak, "Point Mutations Define a Sequence Flanking the AUG Initiator Codon That Modulates Translation by Eukaryotic Ribosomes," *Cell* 44:283–292 (1986).

Kyte, et al., "A Simple Method for Displaying the Hydropathic Character of a Protein," *J. Mol. Biol.* 157:105–132 (1982).

Le Bonniec, et al., "The Role of Calcium Ions in Factor X Activation by Thrombin E192Q," *J. Biol. Chem.* 267(10):6970–6976 (1992).

Ledbetter, et al., "Covalent Association Between Human Thymus Leukemia–like Antigens and CD8(Tp32) Molecules," *J. Immunol.* 134(6):4250–4254 (1985).

Lentz, et al., "Regulation of Thrombomodulin by Tumor Necrosis Factor–α: Comparison of Transcriptional and Post-transcriptional Mechanisms," *Blood* 77(3):542–550 (1991).

Lewis, et al., "Automated site–directed drug design: the concept of spacer skeletons for primary structure generation," *Proc. R. Soc Lond.* 236:125–140 and 141–162 (1989).

Maciag, et al., "An endothelial cell growth factor from bovine hypothalamus: identification and partial characterization," *Proc. Natl. Acad. Sci. (USA)* 76(11):5674–5678 (1979).

Maher, et al., "Inhibition of DNA Binding Proteins by Oligonucleotide–Directed Triple Helix Formation," *Science* 245:725–730 (1989).

Marra, et al., "Mus musculus cDNA clone similar to centrocylin," Accession No. AA016910 (Aug. 3, 1996).

Marra, et al., "Mus musculus cDNA clone," Accession No. AA146223 (Dec. 14, 1996).

Marra, et al., "Mus musculus cDNA similar to M. musculus endothelial cell activated protein C receptor," Accession No. AA389039 (Jun. 25, 1997).

Maruyama, et al., "Increased Expression of Thrombomodulin on the Cultured Human Umbilical Vein Endothelial Cells and Mouse Hemangioma Cells by Cyclic AMP," *Thrombosis Research* 61:301–310 (1991).

McKinlay, et al., "Rational Design of Antiviral Agents," *Annu. Rev. Pharmacol. Toxiciol.* 29:111–122 (1989).

Merrifield, "Solid Phase Peptide Synthesis. I. The Synthesis of a Tetrapeptide," *J. Am. Chem. Soc.* 85:2149–2154 (1963).

Mizushima, et al., "pEF–BOS, a powerful mammalian expression vector," *Nucleic Acids Res.* 18:5322 (1990).

Moore, et al., "Tumor Necrosis Factor Leads to the Internalization and Degradation of Thrombomodulin From the Surface of Bovine Aortic Endothelial Cells in Culture," *Blood* 73(1):159–165 (1989).

Mulligan, "The Basic Science of Gene Therapy," *Science* 260:926–932 (1993).

Narang, et al., "Chemical Synthesis of Deoxylingonucleotides by the Modified Triester Method," *Methods Enzymol.* 65:610–620 (1980).

Nawroth, et al., "Modulation of Endothelial Cell Hemostatic Properties by Tumor Necrosis Factor," *J. Exp. Med.* 163:740–745 (1986).

Offensperger, et al., "In Vivo inhibition of duck hepatitis B virus replication and gene expression by phosphorothioate modified antisense oligodeoxynucleotides," *EMBO J.* 12(3):1257–1262 (1993).

Olsen, et al., "$Ca^{2+}$ Dependence of the Interactions Between Protein C, Thrombin, and the Elastase Fragment of Thrombomodulin, Analysis by Ultracentifugation," *Biochemistry* 31(3):746–754 (1992).

Orson, et al., "Oligonucleotide inhibition of IL2Rα mRNA transcription by promotor region collinear triplex formation in lymphocytes," *Nucl. Acids Res.* 19(12):3435–3441 (1991).

Panja, et al., "CD1d Is Involved in T Cell–Intestinal Epithelial Cell Interactions," *J. Exp. Med.* 178:1115–1119 (1993).

Péléraux, et al., "Genomic organization of a mouse MHC class II region including the H2–M and Lmp2 loci," *Immunogenetics* 43:204–214 (1996).

Perry, et al., "The Use of 3D Modelling Databases for Identifying Structure Activity Relationships," *QSAR: Quantitative Structure–Activity Relationships in Drug Design*, pp. 189–193 (Alan R. Liss, Inc., 1989).

Porcelli, et al., "CD1b restricts the response of human CD4-8- T Lymphocytes to a microbial antigen," *Nature* 360:593–597 (1992).

Postel, et al., "Evidence that a triplex–forming oligodeoxyribonucleotide binds to the c–myc promoter in HeLa cells, thereby reducing c–myc mRNA levels," *Proc. Natl. Acad. Sci. USA* 88:8227–8231 (1991).

Proudfoot, et al., "3' Non–coding region sequences in eukaryotic messenger RNA," *Nature* 263:211–214 (1976).

Regan, et al., "The Endothelial Cell Protein C Receptor," *J. Biol. Chem.* 271(29):17499–17503 (1996).

Rezaie, et al., "The High Affinity Calcium–binding Site Involved in Protein C Activation is Outside the First Epidermal Growth Factor Homology Domain," *J. Biol. Chem.* 267(17):11701–11704 (1992).

Ripka, et al., "Computers Picture the Perfect Drug," *New Scientist* 54–57 (Jun. 16, 1988).

Rothbarth, et al., "cDNA–derived molecular characteristics and antibodies to a new centrosome–associated and $G_2$/M phase–prevalent protein," *J. Cell. Sci.* 104:19–30 (1993).

Rouvinen, et al., "Computer–Aided Drug Design," *Acta Pharmaceutica Fennica* 97:159–166 (1988).

Sarin, et al., "Inhibition of acquired immunodeficiency syndrome virus by oligodeoxynucleoside methylphosphonates," *Proc. Natl. Acad. Sci. USA* 85:7448–7794 (1989).

Seligsohn, et al., "Homozygous Protein C Deficiency Manifested by Massive Venous Thrombosis in the Newborn," *N. Eng. J. Med* 310(9):559–562 (1984).

Semon, et al., "Nucleotide sequence of the murine TNF locus, including the TNF–α (tumor necrosis factor) and TNF–β (lymphotoxin) genes," *Nuc. Acids Res.* 15(21):9083–9084 (1987).

Shaw, et al., "Modified deoxyogligonucleotides stable to exonuclease degradation in serum," *Nucleic Acids Res.* 19(4):747–750 (1991).

Stern, et al., "Cultured Bovine Aortic Endothelial Cells Promote Activated Protein C–Protein S–mediated Inactivation of Factor V," *J. Biol. Chem.* 261(2):713–718 (1986).

Stearns–Kurosawa, et al., "The endothelial cell protein C receptor augments protein C activation by the thrombin–thrombomodulin complex," *Proc. Natl. Acad. Sci. USA* 93:10212–10216 (1996).

Szostak, "In vitro genetics," *TIBS* 19:89–93 (1992).

Taylor, et al., "C4b–Binding Protein Exacerbates the Host Response to *Escherichia coli*," *Blood* 78(2):357–363 (1991).

Taylor, et al., "Protein C Prevents the Coagulopathic and Lethal Effects of *Escherichia coli* Infusion in the Baboon," *J. Clin. Invest.* 79:918–925 (1987).

Von Heijne, "A new method for predicting signal sequence cleavage sites," *Nucleic Acids Res.* 14(11):4683–4690 (1986).

Wickstrom, et al., "Human promyelocytic leukemia HL–60 cell proliferation and c–cym protein expression are inhibited by an antisense pentadecadeoxynucleotide targeted against c–myc mRNA," *Proc. Natl. Acad. Sci. USA* 85:1028–1032 (1988).

Williams, et al., "The Immunoglobulin Superfamily—Domains for Cell Surface Recognition," *Ann. Rev. Immunol.* 6:381–405 (1988).

Young, et al., "Triple helix formation inhibits transcription elongation in vitro," *Proc. Natl. Acad Sci. USA* 88:10023–10026 (1991).

Zamecnik, et al., "Inhibition of Rous Sarcoma Virus Replication and Cell Transformation by a Specific Oligodeoxynucleotide," *Proc. Natl. Acad. Sci. USA* 75:280–284 (1978).

Zamecnik, et al., "Inhibition of replication and expression of human T–cell lymphortropic virus type III in cultured cells by exogenous synthetic oligonucleotides complementary to viral RNA," *Proc. Natl. Acad. Sci.* 83:4143–4143 (1986).

Zhu, et al., "Systemic Gene Expression After Intravenous DNA Delivery Into Adult Mice," *Science* 261:209–211 (1993).

Garlanda et al. Heterogeneity of endothelial cells. Arterosclerosis, Thrombosis, and Vascular Biology. vol. 17(7):1193–1202, Jul. 1997.

Yoder et al. Cytosine methylation and the ecology of intragenomic parasites. Trends in Genetics. vol. 13(8):335–340, Aug. 1997.

Lania et al. Transcriptional regulation by the Sp family proteins. Int. J. Biochem. Cell Biol. vol. 29(12):1313–1323, Jan. 1998.

Orkin et al. Report and recommendations of the panel to assess the NIH investment in research on gene therapy, Dec. 1995.

Verma et al. Gene therapy—promises, problems and prospects. Nature. vol. 389:239–242, Sep. 1997.*

Anderson, W. F. Human Gene Therapy. Nature. vol. 392:25–30, Apr. 1998.*

Marshall, E. Gene therapy's growing pains, Science. vol. 269:1050–1055, Aug. 1995.*

* cited by examiner

```
2993  TCGAAAGCAGAGACGCCCCACCCCCTGACTCAGCGGGCGACCTACCGGACTT  3042
         |  |||||  |||  |||||  ||||||       |  ||||||
2707  TTGAAAGTAGATGCCCCA.CCCCCTGAGTCAGCG....CCGGCAGGACTT  2751

3043  CTCGCCAAGCCCCTTCTCCCCCTTTTCCGCTCC....TCCTCAAGCCTCGG  3088
      |||  ||||||||||||||||||||||||||||    |||   ||   ||
2752  CTCACCAAGCCCCTTCTCCCCCTTTTCCGCTCCCCTGTTCCTGGTTCCTAGG  2801

3089  AAGCAAGCAGGGGAGGAGAAACAGGCAGGTCCAGGCAGGGAGGCCCACA  3138
      |||   |||   |||||||||| ||||||||||||||||    ||
2802  AAGCAGCCCAAGGAGAAGGAGAAAAAGCAGGTCTGGGCAGGAGGAGCAAT  2851

3139  GCTGGGAGGGGC.........CGAGGCGAGCCGGCCCCCTAGTAGGA  3176
       |  |||  ||           ||||          ||||||||||
2852  GAAGGGGCGGGGCAGAGGAGGGGCAGGAGGCAGGCCCCCTAGTAGGA  2901

3177  AATGAGACAGA.TCCAAGTAACACTTTAAAAGCCTGACTCCCCTCTTCCTG  3225
      ||||||| ||| | |||  ||||||||| ||||||  |  |  |
2902  AATGAGACACAGTAGAAATAACACTTTATAAGCCT.CTTCCTCCTCCCAT  2950

3226  CACGCGTTCTCTTTCCATCCTCC...GCTCTGCTCCGGCCCCTCCCGGAC  3272
      |  |  ||||||||||||||||      ||| |||   ||||||  |||
2951  CTCCTGGCCTCCTTCCATCCTCCTCTGCCCAGACTCCGCCCCCTCCCAGAC  3000
```

FIG. 1A

```
3273  AG..CCTCCCTTCTCTTT..CCTAATCAGCAGCCTGAGGAACCCGAGCCTG  3319
         ||||  ||||||||||  ||||   |||| ||| |||| ||| ||||
3001  GGTCCTCACTTCTCTCTTTTCCCTAGACTGCAGCCAGCGGAGCCCGAGCCG  3050

3320  CCCCGACCCAGG........TGGGACCCAGAACTCCAGGATGTTGACGA    3360
      ||||| |||||         |||  ||  ||||  |||||||||||| |
3051  GCCCGAGCCAGGAACCCAGGTCCGAGCCTCAACTTCAGGATGTTGACAA    3100

3361  AGTTTCTGCCGCTACTGCTGCTGCCCCTTTGTA..                 3408
       ||  |||||||    |||||| ||||  ||||
3101  CATTGCTGCCGATA........CTGCTGCTGTCTGGGCCTTTTGTAGC    3144

3409  ........ACTCCGATGGTGAGTTTGGGTCAAGGCTCCTGCCTGGGGGT.G  3450
              |||  |||||||||||||   ||  ||||||||  ||||||  |
3145  CAAGAGCCCTCAGATGGTGAGTCGGTGGGGGCACATCTCCTGCCTCAGGATGG  3194

3451  TTCTAGGGA...CTTGGTGTATTTGGGAACTTTG                   3481
      ||||  ||    || ||  ||  |||  |||||
3195  TTCTGGAGAATCTCAGTCTATCTGGGCACATGG                    3227
```

ENDOTHELIAL SPECIFIC EXPRESSION REGULATED BY EPCR CONTROL ELEMENTS

This application claims the benefit of U.S. Provisional application Ser. No. 60/030,718 filed Nov. 8, 1996, by Charles T. Esmon, Wei Ding, Jian-Ming Gu and Kenji Fukudome, entitled "Thrombin Response Element", and U.S. Ser. No. 60/054,533 filed Aug. 4, 1997 by Charles T. Esmon and Jian-Ming Gu, entitled "Endothelial Specific Expression Regulated by EPCR Control Elements".

The United States government has certain rights in this invention by virtue of National Heart, Lung and Blood Institute of the Institutes of Health grant No. P01 HL54804 to Charles T. Esmon.

BACKGROUND OF THE INVENTION

The present invention is generally in the area of targeting and regulation of expression of recombinant gene constructs incorporating regulatory elements present in the promoter of an endothelial cell protein C/activated protein C receptor.

Atherosclerosis and most other vascular disease primarily occur in large vessels. Endothelial cells are a primary defense mechanism against cellular infiltration and thrombosis. Abnormal function of the endothelial cells contribute to myocardial infarction (MI), stroke and the development of atherosclerotic plaque. The delivery of proteins or protein expression inhibitors, directly or via gene therapy, specific to large vessel endothelial cells, is one means for addressing these clinical conditions. For example, the anti-thrombotic potential of endothelium can be increased by delivering agents that prevent thrombosis, such as thrombomodulin, heparin proteoglycans, tissue factor pathway inhibitor (TFPI, a potent inhibitor of the tissue Factor-Factor VIIa-Factor Xa complex), etc. Fibrinolytic activity can be increased by overexpression of tissue plasminogen activator (tPA) or urokinase. Expression of adhesion molecules such as P-selectin or ICAMs can be inhibited to minimize or decrease the probability of atherosclerotic plaque rupture.

Targeting endothelial cells non-specifically is often inadequate. Since more than 95% of endothelial cells are in the capillaries, any therapy directed toward endothelial cells per se runs the risk of systemic complications. One must be confident that the gene expression is limited to the desired cells when using a gene therapy approach.

It is therefore an object of the present invention to provide means and methods for selective expression of genes, especially in endothelial cells, and even more specifically in large vessel endothelial cells.

It is a further object of the present invention to provide means and methods for selective expression of genes in response to specific stimuli.

SUMMARY OF THE INVENTION

The promoter of the EPCR gene has been isolated from both murine (SEQ. ID No. 1) and human (SEQ. ID No. 2) genomic libraries. The promoter has been demonstrated to include a region which results in selective expression in endothelial cells, between −1 and −220 based on the positions relative to the ATG encoding the first amino acid of the murine EPCR protein (nucleotides 3130 to 3350 of SEQ. ID No. 1), and a region which selectively results in expression in large vessel endothelial cells, as opposed to all endothelial cells, located between −700 and −1080 (nucleotides 2270 to 2840 of SEQ. ID No. 1). A thrombin responsive element has been identified in the EPCR promoter, from −337 to −345 in the murine promoter (nucleotides 3007 to 3014 SEQ. ID No. 1) and from −360 to −368 (nucleotides 2722 to 2729 SEQ. ID No. 2) in the human promoter. The sequence is CCCAC-CCC (SEQ. ID No. 3). A serum response element has also been identified between −280 and −350 (nucleotides 2990 to 3061 of SEQ. ID No. 1).

The regulatory sequences present in the EPCR promoter can be used in combination with genes encoding other proteins, as well as shorter oligonucleotides, to increase expression by exposure to thrombin or serum or to effect selective expression in endothelial cells generally or preferentially in endothelial cells of the large blood vessels. The gene control elements include elements responsive to environmental stimuli (either thrombin or serum); and information to determine distribution of the desired protein expression (large vessels). Therapeutic strategies include the use of the minimal promoter (−220 to −1) for expression in all endothelial cells, for example, for any kind of gene therapy where systemic distribution is desired; the use of a promoter including an environmental stimuli response element(s), for use in delivery of agents whose expression should be increased during times of increased thrombin/platelet activation or during regional trauma; the use of the minimal promoter including an environmental stimuli response element and the element directing expression to large vessel endothelium, where a response to regional trauma is desirable but only in large vessel endothelium, and the use of the minimal promoter and element directing expression to large vessel endothelium, where expression is specifically targeted to large vessel endothelium but is not increased in response to any particular stimuli.

BRIEF DESCRIPTION OF THE DRAWING

FIG. 4 is a schematic of the promoter. The top line indicates the structure of the promoter from −220 to −177, (showing nucleotides 3120 to 3157 of SEQ ID No. 1) which includes the transcription control elements required for constitutive expression in endothelial cells (nucleotides 3120 to 3156 of SEQ ID No. 1). AP4 and SP-1 are known promoter elements that bind proteins that control gene expression. The bottom line is a schematic representation of the EPCR promoter showing the locations of the large vessel specific element between −1080 and −700 ("C"), the element which includes the sequence responsible for thrombin induction ("B"), the endothelial specific region ("A"), and the EPCR encoding element. SP-1, AP-1 and AP-4 are known promoter elements which bind proteins involved in transcription control.

DETAILED DESCRIPTION OF THE INVENTION

Specific targeting of expression of desired genes can be achieved through the selection and use of the regulatory sequences described herein in detail, isolated from the protein C receptor (EPCR). The protein C receptor is the first protein identified and reported with these properties. It is expressed in high levels exclusively in large vessels, and the expression levels decrease with vessel size, until there is little-to-no expression detectable in capillaries.

The EPCR Regulator Sequences

The endothelial cell protein C binding protein (referred to herein as "EPCR") was cloned and characterized, as described in PCT/US95/09636 "Cloning and Regulation of an Endothelial Cell Protein C/Activated Protein C Receptor" Oklahoma Medical Research Foundation. The protein was predicted to consist of 238 amino acids, which includes a 15 amino acid signal sequence at the N-terminus, and a 23 amino acid transmembrane region which characterizes the receptor as a type 1 transmembrane protein. The protein binds with high affinity to both protein C and activated protein C (Kd=30 nM), which is a naturally occurring anticoagulant, and is calcium dependent.

Following identification and cloning of the endothelial cell protein C receptor (EPCR), it was determined that the EPCR was down regulated in cultured endothelial cells by TNFα. To determine the physiological relevance of this finding, EPCR mRNA levels in rats and mice challenged with $LD_{95}$ levels of endotoxin were examined. Surprisingly, in response to endotoxin infusion, EPCR message rose within three hours to about four fold the basal level and remained elevated for twelve hours, then returning toward baseline at 24 hours. The rapid response suggested that a factor generated by endotoxin infusion could upregulate EPCR expression. Since thrombin is known to be one of these factors, rat microvascular cells in culture were treated with thrombin (0.1 units/ml). The cells exhibited a three to four fold increase in EPCR mRNA levels within three hours relative to control cells.

Physiologically, these results showing elevated mRNA levels three hours after exposure to thrombin, which begins to decline after twelve hours to baseline levels by 24 hours, are important since they suggest that thrombin plays a direct in vivo role in upregulation of EPCR expression. High level EPCR expression could contribute to the decrease observed in protein C levels during acute inflammatory response syndromes.

The gene encoding EPCR including the promoter region was then isolated from a murine genomic library, using the DNA encoding murine EPCR as a probe. A human genomic library was similarly screened with the DNA encoding human EPCR to isolate the promoter for the human EPCR Analysis of the promoter revealed a thrombin response element. Gel shift assays revealed that thrombin treatment induced at least one factor that binds specifically to this promoter region. Further analysis yielded the sequence of the thrombin responsive element. This element can be used to increase selective expression in response to thrombin. The promoter is also selective in expression, with the EPCR being selectively expressed more in large vessel endothelial cells when most of the entire promoter is present, including the beginning region. When a shorter portion of the promoter is present, there is expression in all endothelial cells. These results are consistent with a repressor being present in the first part of the promoter which suppresses expression in capillary endothelial cells.

Figure 1A:
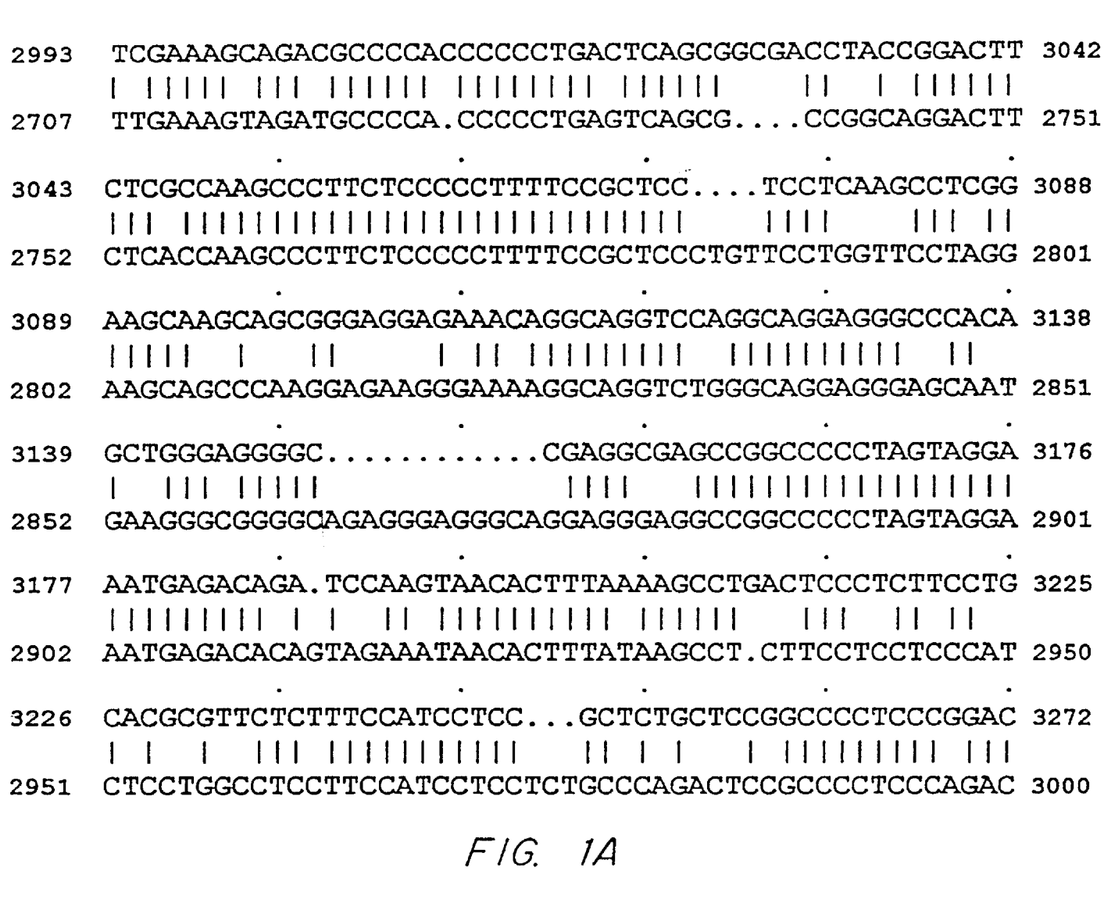
FIGS. 1A–1B are a comparison of the nucleotide sequences of the murine EPCR (nucleotides 2993 to 3481 of SEQ ID No. 1) and human EPCR promoters (nucleotides 2704 to 3224 of SEQ. ID No. 2).
Figure 1B:
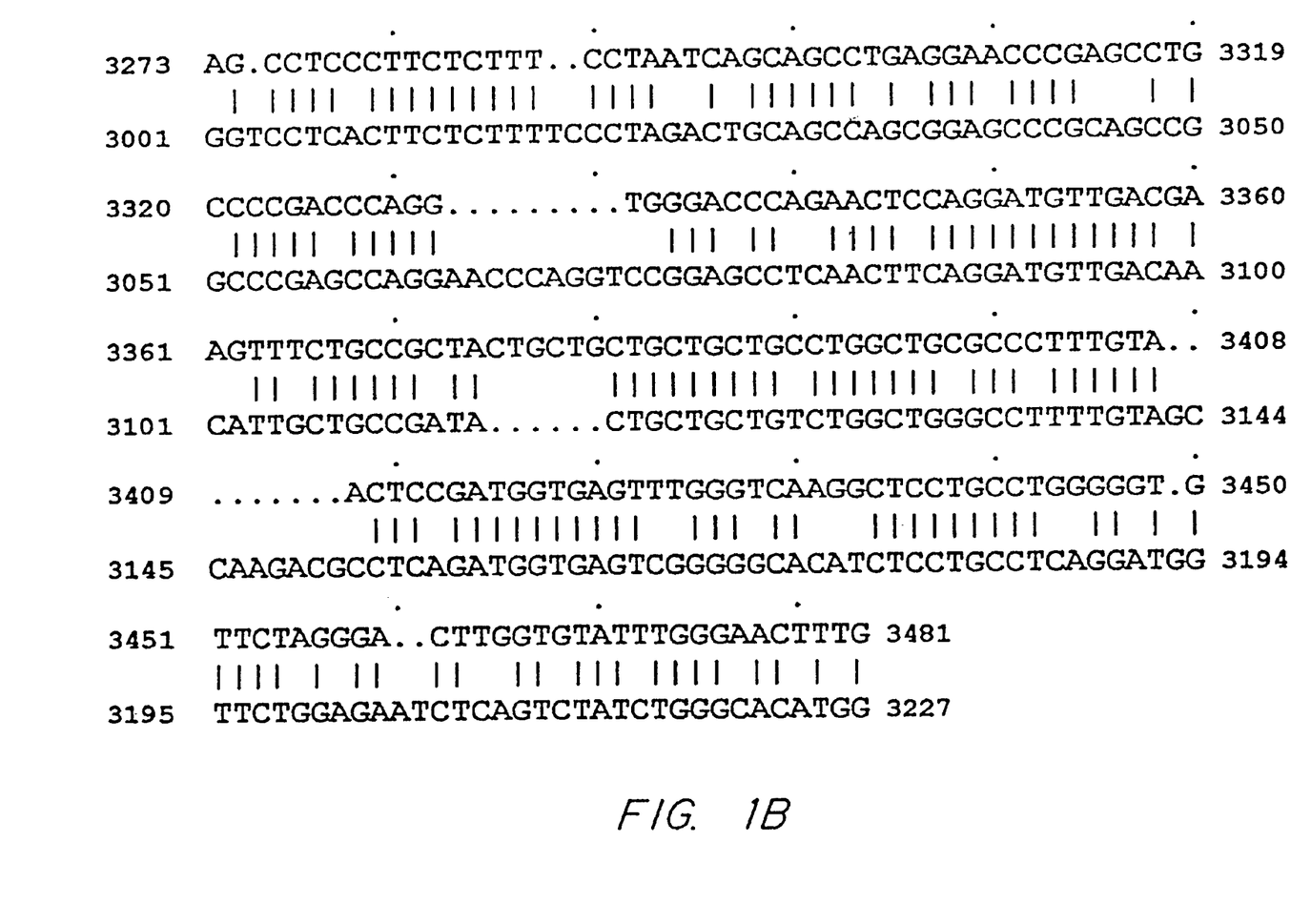

Referring to FIGS. 1A–1B and SEQ. ID Nos 1 (the murine EPCR promoter) and 2 (the human EPCR promoter), the 5' regulatory sequences of the EPCR includes a transcription initiation promoter specific to endothelium contained in −1 to −220 (nucleotides 3130 to 3350 of SEQ. ID No. 1) (referred to for ease of reference as "A"), a control element responsive to thrombin (CCCACCCC) (SEQ. ID No. 3) located between −337 and −345 in the murine promoter (nucleotides 3007 to 3014 of SEQ ID No. 1) and between −360 and −368 in the human promoter (nucleotides 2722 to 2729 of SEQ. ID No. 2) (referred to as "B"), a serum response element located between −280 and −350 (nucleotides 2990 to 3061 of SEQ. ID No. 1) (referred to as "D"), and a large vessel expression element located between −1080 and −700 (nucleotides 2270 to 2840 of SEQ. ID No. 1) (referred to as "C"). The latter directs expression primarily to large vessels such as aorta, coronary arteries, arteries and veins, rather than to capillaries.

FIGS. 1A–1B are a comparison of the sequences from the murine and human promoters, demonstrating that they are highly homologous. It is understood that the equivalent regions from the promoters of EPCR from other species could be used to achieve the same type of expression, and that sequences from different species could be used in combination, for example, A from the murine promoter and C from the human promoter.

Expression Constructs

These regulatory elements can be used alone or in various combinations, as demonstrated by the examples, to determine where and to what extent expression is obtained, both in vitro and in vivo. Region A can drive endothelial cell specific expression. Adding to this region A, region C would result in expression occurring primarily in large vessels. Adding region B to these regions A and C, results in a thrombin response- i.e., expression is increased by exposure to thrombin, as would occur in a patient during initiation of coagulation or an inflammatory response.

The regulatory sequences can be inserted into vectors for expression using standard recombinant techniques.

The Regulatory Elements are useful as Reagents

The nucleotide sequences are important as hybridization probes, in selected expression of recombinant proteins other than EPCR, in increasing expression of recombinant proteins by exposure of the encoding construct to thrombin, and in design and screening of drugs and diagnostics for therapeutic and research purposes.

Methods of Treatment

The constructs are particularly useful in gene therapy. The elements can be used to regulate expression of a gene encoding an important protein, or a biologically active nucleic acid molecule such as antisense, triplex forming molecules, ribozymes, and guide sequences for RNAase P which can be used to mutate or stop transcription of a particular gene. Examples of gene targeting include expression of thrombomodulin (TM), EPCR, TFPI, tPA, or heparin (heparan proteoglycans) in large vessel endothelium to decrease clot propensity at atheromas or in autoimmune diseases. If systemic elevations of tPA was desired, sequence A could be used on the gene. Endogenous gene expression could be suppressed by using sequence A, ABC or possibly AC, coupled to antisense to block expression of adhesion molecules to decrease leukocyte infiltration in atherosclerosis. The thrombin response element is significantly inducible in vivo, and should therefore be particularly useful in the treatment of patients with a history of constitutively elevated levels of thrombin, for example, particularly for expression of therapeutic genes in coronary arteries in patients with unstable angina.

The present invention will be further understood by reference to the following non-limiting examples:

Example 1: Isolation of Endothelium and Large Vessel Endothelium Specific Transcription Initiator Elements.

Nucleotide sequences were determined for 8.8 kb of the genomic structure and 3.4 kb of the 5'-flanking region of the mouse EPCR (mEPCR) gene. RNase protection assay revealed six major transcription start sites clustered at −110 to −119 upstream of the translation initiation site. A series of 5'-promoter deletion fragments: mP3340, mP1120, mP700, mP350 and an SV40 control were fused to a luciferase reporter gene and transiently transfected into several cell types, bovine aorta endothelial cells (large vessel endothelial cells), rat heart endothelial cells which is mostly capillary endothelial cells (small vessel endothelial cells), and 293 kidney cells (non-endothelial cells).

Figure 2:
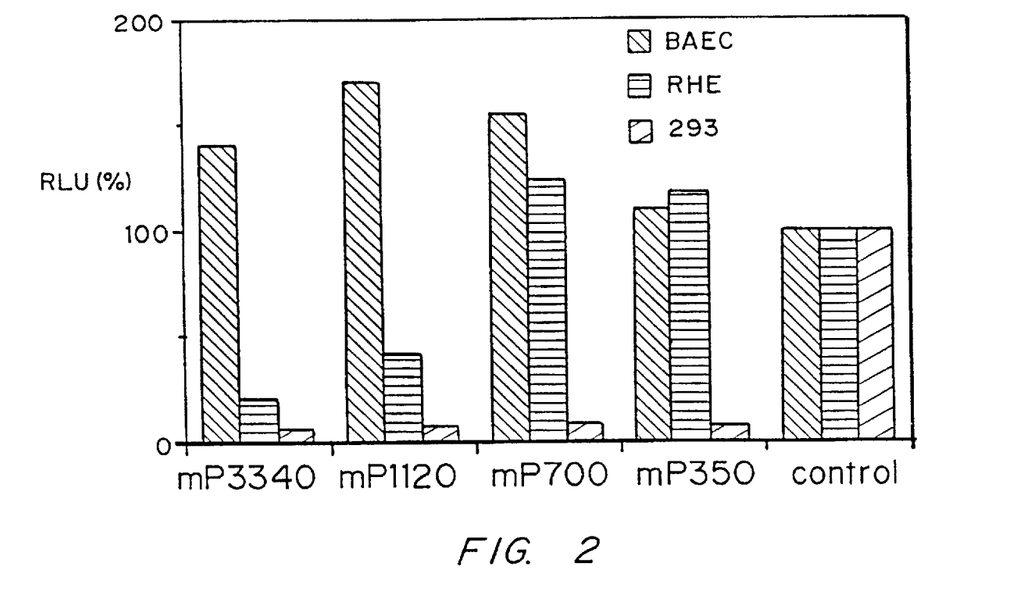
FIG. 2 is a graph of relative levels of expression (relative luminescent units) for mP3340, mP1120, mP700, mP350 and control SV40, in bovine endothelial cells (large vessel endothelial cells; BA EC), rat heart endothelial cells which are mostly capillary cells (small vessel endothelial cells; RHE), and 293 kidney cells (nonendothelial cells; 293).

The results are shown in FIG. 2. The expression was relatively endothelial cell specific.

Figure 3:
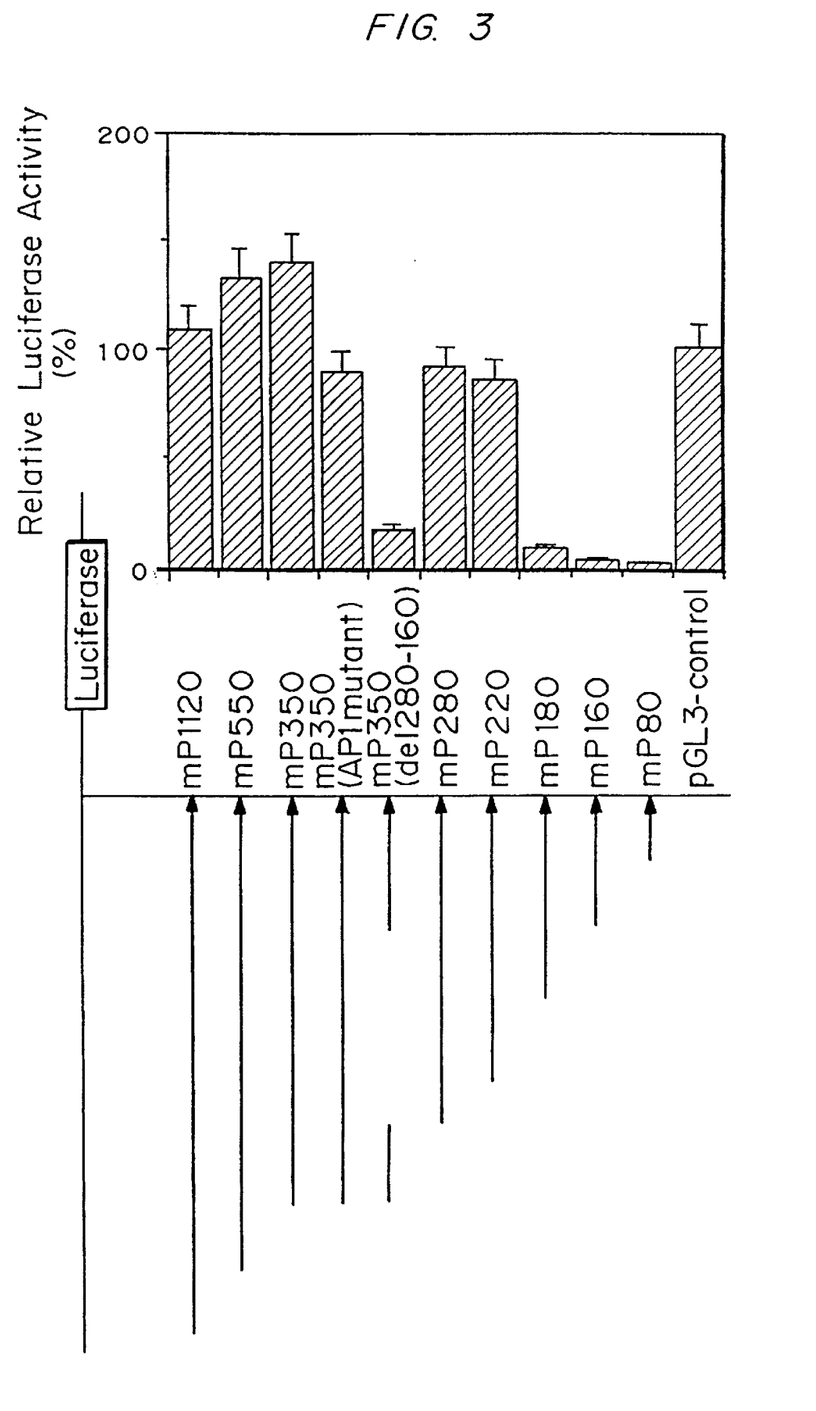
FIG. 3 is a schematic of the constructs transfected into bovine aortic (large vessel) endothelial cells, graphing the relative levels of expression (relative luminescent units) for mP1120, mP550, mP350, mP350 (AP1 mutant), mP350 (deletion from 280 to 160), mP280, mP220, mP180, mP160, and mP80, with the pGL3 control.
Figure 4:
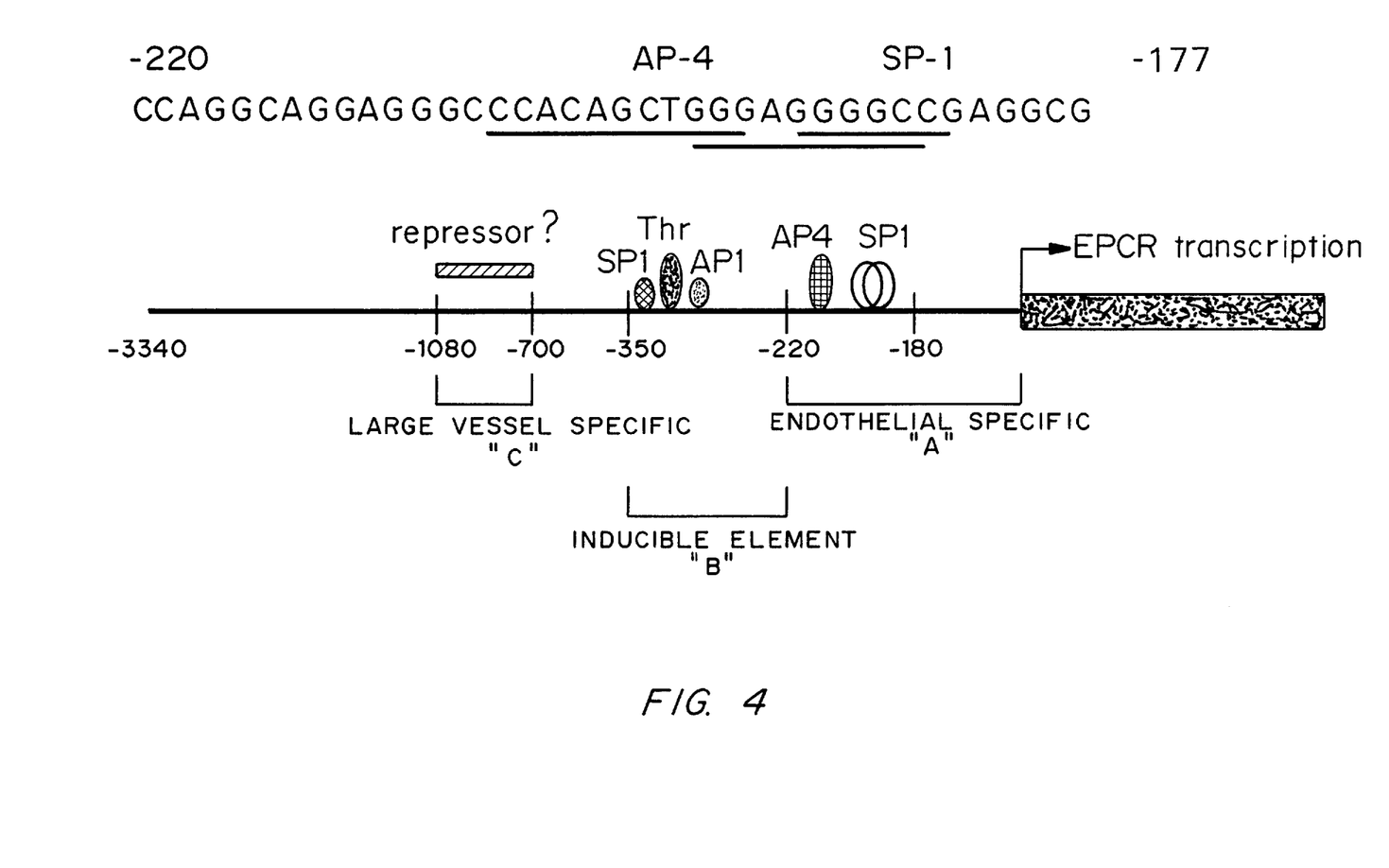

Deletion of the sequence between −280 to −160 dramatically reduced luciferase expression in bovine aorta cells, as shown by FIG. 3. This region of the mEPCR gene (−220 to −180) contains one AP-4 site and two overlapping SP-1 sites, as depicted in FIG. 4. Mutations in the core sequence of the AP-4 site and two overlapping SP-1 sites impaired both nuclear protein binding and luciferase expression. These results indicate important roles for AP4 and SP-1 in the constitutive expression of mEPCR.

Example 2: Thrombin Response Element.

A thrombin response element (CCCACCCC) (SEQ. ID No. 3) within the upstream region (−337 to −343) was found to mediate the induction of mEPCR by thrombin. In addition, a 380 bp fragment which spans the sequences from −1080 to −700 was identified as the endothelial cell-type specific promoter in cultured cells. This fragment could drive expression of luciferase or green fluorescent protein in large vessel endothelium but not in microvascular or capillary cells, as also shown by FIG. 2.

Example 3: In vivo Activity of the EPCR Promoter.

Transgenic mice were developed using either the −350 to −1 or −1080 to −1 regions of the mouse EPCR promoter to drive the structural gene for green fluorescent protein (GFP) to determine the in vivo activity of the previously described promoter regions.

The promoter regions (−1080 and −350) of mouse EPCR gene were cloned into the pEGFP1 vector (Clontech), which already contains the structural gene for GFP. The fragments which contained the promoter region of mEPCR and GFP reporter gene were released by enzymes Eco47 III and Afl II from the constructs pEGFP350 and pEGFP1080. After purification, the DNA fragments were microinjected into the pronuclei of fertilized mouse eggs by standard methods. Mice were screened for the presence of the transgene by GFP specific PCR and Southern blotting by standard methods. Several transgenic lines were established from both promoter constructs.

GFP mRNA was constitutively expressed in these lines. The level of GFP mRNA expression was variable from significantly less than to higher than the endogenous EPCR expression. These data indicate that the ability to express a foreign structural gene under the control of these promoters will not be chromosome integration position dependent, although constitutive level of expression may be influenced by chromosomal positioning.

Example 4: LPS Inducibility of the EGFP1080 and EGFP350 Constructs in Transgenic Animals Animals bearing the EGFP1080 construct and animals bearing the EGFP350 construct were treated with 400 micrograms LPS for 3 hours. Quantitative RT-PCR was performed to determine the level of GFP mRNA present before and after induction. GFP and mEPCR MIMICs (500 bp in length) were prepared by use of the MIMIC construction kit (Clontech). 2 micrograms of total RNA from the mice was used for synthesis of cDNA. Equal sized aliquots were then amplified in the presence of 2 microliters of a 10-fold dilution series of the appropriate MIMIC=(GFP or mEPCR). Equal aliquots were then run on a 2% ethylene bromide agarose gel. The target size is 300 bp and the MIMIC is 500 bp. The ability of the bonafide message to compete for its "MIMIC" at a particular dilution of the MIMIC indicates the abundance of the message in the original sample. Before LPS induction, the GFP mimic could not be effectively competed by the animal's mRNA until the mimic was diluted 1:100,000 for the P1080 animal and 1:106 for the P350 animal. After 3 hr treatment with 400 micrograms LPS, the EGFP1080 animal expressed at least ten times more message (mimic is effectively competed at a 1:10,000 dilution). The EGFP350 animal could at least partially compete at the same level.

The finding that expression can be induced by treatment of the animals with endotoxin indicates that the response elements are functional in vivo, and with heterologous proteins.

Modifications and variations of the methods and materials described herein will be obvious to those skilled in the art from the foregoing detailed description, and are intended to come within the scope of the appended claims. In particular, further definition of the minimal regulatory elements using standard approachs similar to those described herein would be considered obvious equivalents.

---

We claim:

1. An isolated naturally occurring cell specific regulatory element present in the endothelial protein C receptor promoter which directs expression to human, bovine, rat or murine endothelial cells, wherein said regulatory element is contained in nucleotides 3130 to 3350 of SEQ ID NO:1 or is contained in nucleotides 2868 to 3087 of SEQ ID NO:2.

2. The regulatory element of claim 1 which is contained in nucleotides 3130 to 3350 of SEQ ID NO:1.

3. The regulatory element of claim 1 which is contained in nucleotides 2868 to 3087 of SEQ ID NO:2.

4. An isolated naturally occurring tissue specific regulatory element present in the endothelial protein C receptor promoter which preferentially directs expression to human, bovine, rat or murine large vessel endothelial cells, wherein said regulatory element is contained in nucleotides 2270 to 2840 of SEQ ID NO:1 or is contained in nucleotides 2008 to 2388 of SEQ ID NO:2.

5. The regulatory element of claim 4 which is contained in nucleotides 2270 to 2840 of SEQ ID NO:1.

6. The regulatory element of claim 4 which is contained in nucleotides 2007 to 2387 of SEQ ID NO:2.

7. An isolated inducible regulatory element present in the endothelial protein C receptor promoter which is inducible by exposure to serum wherein said regulatory element is contained in nucleotides 2990 to 3061 of SEQ ID NO:1 or is contained in nucleotides 2738 to 2808 of SEQ ID NO:2.

8. The regulatory element of claim 7 which is contained in nucleotides 2990 to 3061 of SEQ ID NO:1.

9. The regulatory element of claim 7 which is contained in nucleotides 2727 to 2798 Of SEQ ID NO:2.

10. A construct for expression of a gene comprising a regulatory element selected from the group consisting of an isolated naturally occurring regulatory element present in the endothelial protein C receptor promoter which directs expression to human, bovine, rat or murine endothelial cells, which is contained in nucleotides 3130 to 3350 of SEQ ID NO:1 an isolated naturally occurring regulatory element present in the endothelial protein C receptor promoter which preferentially directs expression to human, bovine, rat or murine large vessel endothelial cells, which is contained in nucleotides 2270 to 2840 of SEQ ID NO:1, or which is contained in nucleotides 2008 to 2388 of SEQ ID NO:2, and an isolated regulatory element present in the endothelial protein C receptor promoter which is inducible by exposure to serum, which is contained in nucleotides 2990 to 3061 of SEQ ID NO:1 or is contained in nucleotides 2738 to 2808 of SEQ ID NO:2.

11. The construct of claim 10 further comprising a heterologous gene.

12. The construct of claim 10 further comprising a thrombin response element which is SEQ ID No. 3.

13. The construct of claim 10 wherein the regulatory element comprises an isolated regulatory element present in the endothelial protein C receptor promoter which directs expression to human, bovine, rat or murine endothelial cells, which is contained in nucleotides 3130 to 3350 of SEQ ID NO:1, or which is contained in nucleotides 2868 to 3087 of SEQ ID NO:2, and an isolated regulatory element present in the endothelial protein C receptor promoter which preferentially directs expression to human, bovine, rat or murine large vessel endothelial cells, which is contained in nucleotides 2270 to 2840 of SEQ ID NO:1 or which is contained in nucleotides 2008 to 2388 of SEQ ID NO:2.

14. The construct of claim 13 further comprising the thrombin response element which is SEQ ID No. 3.

15. A method for controlling the expression of a gene comprising expressing the gene under the control of a regulatory element selected from the group consisting of an isolated naturally occurring regulatory element present in the endothelial protein C receptor promoter which directs expression to human, bovine, rat or murine endothelial cells, which is contained in nucleotides 3130 to 3350 of SEQ ID NO:1, or which is contained in nucleotides 2868 to 3087 of SEQ ID NO:2, an isolated naturally occurring regulatory element present in the endothelial protein C receptor promoter which preferentially directs expression to human, bovine, rat or murine large vessel endothelial cells, which is contained in nucleotides 2270 to 2840 of SEQ ID NO:1, or which is contained in nucleotides 2008 to 2388 of SEQ ID NO:2, and an isolated regulatory element present in the endothelial protein C receptor promoter which is inducible by exposure to serum, which is is contained in nucleotides 2990 to 3061 of SEQ ID NO:1 or which is contained in nucleotides 2738 to 2808 of SEQ ID NO:2.

16. The method of claim 15 wherein the gene is also expressed under the control of a thrombin response element which is SEQ ID No. 3.

17. The method of claim 15 wherein the gene is expressed under the control of an isolated naturally occurring regulatory element present in the endothelial protein C receptor promoter which directs expression to human, bovine, rat or murine endothelial cells, which is contained in nucleotides 3130 to 3350 of SEQ ID NO:1, or which is contained in nucleotides 2868 to 3087 of SEQ ID NO:2, and an isolated regulatory element present in the endothelial protein C receptor promoter which preferentially directs expression to human, bovine, rat or murine large vessel endothelial cells, which is contained in nucleotides 2270 to 2840 of SEQ ID NO:1, or which is contained in nucleotides 2008 to 2388 of SEQ ID NO:2.

18. The method of claim 15 wherein the gene encodes a protein.

19. The method of claim 15 wherein the gene is introduced in vitro into cells of a patient in need of treatment thereof.

20. The method of claim 15 wherein the gene is expressed in cell culture.

21. The method of claim 15 wherein the gene encodes a biologically active nucleic acid molecule.

22. The method of claim 19 wherein the biologically active nucleic acid molecule is selected from the group consisting of antisense, triplex forming molecules, ribozymes, and guide sequences for RNAase P.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 3481 base pairs
      (B) TYPE: nucleic acid (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (D) OTHER INFORMATION: /note= "Nucleotides 2270 through
            2840 are a large endothelial specific element"; murine (ix) FEATURE:
        (A) NAME/KEY: misc_feature
        (D) OTHER INFORMATION: /note= "Nucleotides 2990 through
            3061 are a serum response element"; murine (ix) FEATURE:
        (A) NAME/KEY: misc_feature
        (D) OTHER INFORMATION: /note= "Nucleotides 3007 through
            3014 are a thrombin responsive element"; murine (ix) FEATURE:
        (A) NAME/KEY: misc_feature
        (D) OTHER INFORMATION: /note= "Nucleotides 3130 through
            3350 are an endothelial specific element"; murine (xi) SEQUENCE DESCRIPTION: SEQ ID NO:1:

```
AAGCTTTACT CTGCCACATT TCTTCTGCCC GGCCCAGGAT GTAGGCCTCT TTATTAACCA      60

ATCTGGGATC ACTTGTTGTT GGGGGTGGGG TCAAGGTTTA CAGAGCATCA TTTGGTATAT     120

ATGAGCATCT CCTCTTTAGG GAAAACCAGA TCTTGAGGAG CCAATATTTA ATATTTAAGT     180

TTATAGCAGC ACCAGACCAG CCTCACACAC ATATACTCAC ACACACACAC ACACACACAC     240

ACACACACAC ACACATGTAT ATATGTGTGT GTGTATACTC ATTCCGTAAG TTTTGTATAT     300

GTAGTAGATA TGTATATAGT CATTCCATAA GTTCTACGAC CCTGAAGAAC CCTGACTAAT     360

ACACTGCTGT ATTGTTTAGG ATGCGTGCAT AGATGGTATA GTTATACAGA AATGCAAAGA     420

AATGGAAATA GTCAACTTTT ATTTTCATAT GATGTTATAA ATTCAGAGAT CAACGCAGGG     480

GAGAGAGCTA CAACAGAAGA TGAGTTGATG TAGCTTCAGT TACATTTGTC ATGTTGAATC     540

TCTTCTGGGC AGTGGGGATA GATGTGTTTA GAATGCAATT CTACAAACGT GAGGTAATGA     600

TTCTTCAAAT ACAAGACCAT GCACTTAGCT GTGATTTGAA TCCCTCCACG TTGAGGGCTC     660

ATTCGTCTCT CCAGGATGGG CTGGGGAGTC TGCAGTAGCA GAGAAGTGAG CATGGCATGC     720

TTACAAATAC AGCTCAGAGA ACAGGAGCCT GTGCACTGCC ACTGTGACAC CAAGAAGGAT     780

ATAAAGAGTT AAAATTCCTC TATTGGTGCT TGACCCACGC CTGTGCCCCA GAGACAACCT     840

TGAGCCACAG TTGGCCTGCA GACATTCTCC TGTGTGTTTG AACAGACATA GTTAGGAGAT     900

GTGAGGATGG AATTATAAAT GTATTACCTA AACAGGAGTA ATTCTTAATA CAACATGGGA     960

CACACCATCC GTATTTGGTC CATATCCTGC TGCCCCATCA TGGCTCATCG ATCCTTCCGG    1020

TTCTACCCCC CTCTCCCACA CCACTCTTCT AGTACAGGGG TGTACCATTA CCTGTTATTT    1080

GAAATTCTTG TTTTTAACTA AGTAGGAAAT ATATGATCAT ATTCTAGATG TAAAATTAAC    1140

TATTTAAGAC AATTATATTT ATAATGAGAA AAACCCTTTG CAAAATAGTG ACAAAAGTTT    1200

TCACAAGATT TCCCACTCTT CTCTGCTGTC TCAGTCTCTC CCCCCCACCC CATCTCCCTC    1260

TCTCTCCCTC TCCTTCCCTC TCCTCCCCTC TCTTCCCGTC CCCAGAAATA AACCATTGCT    1320

CTACCTAATA CACAGGCTTC TATATTCATT TGCTGCTTAC AGAGACAAGT GTGCTTGGTT    1380

GTTTGTGGAT GAATAGATGG TTCTAAGCTG TATCTAGTGG TCTATAACTT ACTCCTAGAG    1440
```

```
ATGTGTGCAC TGCATGCCAA CCTCCTTCTG TCTTCTAGCT GATGTTTCTG TGTGACGTGT       1500

ACCACTGAAT CAGCATGGAG CAAGATAGCC AGCCTCCCTA TTCCCATGGG GCTTGCCATT       1560

TTGGTGGGAA ATTCAGACAA CAAACATGTG AACAAGTACT ACAGCTTCAA GTGACTCTAA       1620

GCAATATGAA ATGAAGTAGC GGTTTTGCGA GGGAAGATTT TTGGTTTTGT TTTTATTTCT       1680

AAGTAGTATT TTTACCATAG GGGCTTTCCT AACTTGAGAG ACTGACTTTA AACCAAGCTA       1740

CTTACTTCCT AAATAATATC CGAGCTACAC ACGGCTGTCC AAAACCCATC ACAGAAACAT       1800

ACCCGCACGT CATCAATTCA GGAATGGATA AAGAGCATGT GGCATATAAG CTCTATGAGA       1860

CTCTAGGCAA AGGGGGAGGT TAAATTGTAA CATTTTCAAG AAAACAAATG AAACTGTAGG       1920

TCAGCCTGTT AAGTGAATTA ACTAGATTCG GAAAGTCAAA TACTGCATGT TCTCACTCAT       1980

ATGTGGAAGC TAGGGGTGTG TGTGTGCATT CACACATGTA AGCGTGTGTG TCTGGGAGGA       2040

TATCTAAGAA CAAAGTATAA ATATATATAT ACATACATAT ATACACATAT ATGTATATAC       2100

GTATATGTAT ATTTACATAC ATATACATAC ACACACACAT ATATGTGTGT GTGTGTATGT       2160

GTATATATAT GCCATAATGA AACCCCTTAC TATACATACT AACTTAAAAA GTATAAGATA       2220

CTGGTCATGG TGGCTGATAT CTTGAATCCC AGCACTCAGA AGGCAGGGTA AGTTGGAGCT       2280

CTGTGAGTTC AAAGCCAACC TCATATGGAT AGTAAGACCC TGTTTGGGTT TTTATGGTTT       2340

TTTGGGTTTT TTTTTGGTTT TTTTGGGTGT TTGTTTTGT TTTTTTGTTT TTGTTTTTGT        2400

TTTTTGAGAC AGGGTTTTTC TGTGTAGCCC TGGCTGTCCT GGACTCACTC TGTAGGCCAG       2460

GCTGGCCTCA AACTCAGAAA TCCACCTGCC TCTGCCTCCC AAGTGCTGGG ATTAAAGGCG       2520

TGTGCCACCA CGCCCGGCTT TTTTTTTTTT TTTTAAAGTT GAAAATGCAC AGACAGAAAC       2580

GTCCTTATAT ATAAGTGAAC ACATATTTCA GGAAATATTG CTTACTAAGG ATGATGCATC       2640

AAATTTCTTA TTCTGTCCTA CTTCATTTTT TCAAAAGACA TACTAATTTG TGATGTCATT       2700

GCCACTAAAT GACTATGACC TGTCCGATGC TGAGATTTAT CTAGAGCGTT CCTAAATCTC       2760

TGCCACAATG AACTCTTTTT TACTCACTCG ACTCTGTGAC TATTTCTGAG AGCCCCTCTC       2820

CTCCAGTTGT GTAATTCCTG TGTACTTAAA CTTCTGATAA ACTATAGGCA GTTATCCTGG       2880

AAAGTTAGAT TCCAATCCTG GATCTGCCGT CATCGGGACG TACAAACTTT GGGCAAATCC       2940

CTACATCTCT TTTGACCTCA GTTTCCCCGT CATCTCTACA GAGTCGGCAA CATCGAAAGC       3000

AGACGCCCCA CCCCCCTGAC TCAGCGGCGA CCTACCGGAC TTCTCGCCAA GCCCTTCTCC       3060

CCCTTTTCCG CTCCTCCTCA AGCCTCGGAA GCAAGCAGCG GGAGGAGAAA CAGGCAGGTC       3120

CAGGCAGGAG GGCCCACAGC TGGGAGGGGC CGAGGCGAGC CGGCCCCCTA GTAGGAAATG       3180

AGACAGATCC AAGTAACACT TTAAAAGCCT GACTCCCTCT TCCTGCACGC GTTCTCTTTC       3240

CATCCTCCGC TCTGCTCCGG CCCCTCCCGG ACAGCCTCCC TTCTCTTTCC TAATCAGCAG       3300

CCTGAGGAAC CCGAGCCTGC CCCGACCCAG GTGGGACCCA GAACTCCAGG ATGTTGACGA       3360

AGTTTCTGCC GCTACTGCTG CTGCTGCTGC CTGGCTGCGC CCTTTGTAAC TCCGATGGTG       3420

AGTTTGGGTC AAGGCTCCTG CCTGGGGGTG TTCTAGGGAC TTGGTGTATT TGGGAACTTT       3480

G                                                                      3481
```

(2) INFORMATION FOR SEQ ID NO:2:

(i) SEQUENCE CHARACTERISTICS:
        (A) LENGTH: 3224 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: misc_feature
    (D) OTHER INFORMATION: /note= "Nucleotides 2272 through
        2729 are a thrombin responsive element"; Human (xi) SEQUENCE DESCRIPTION: SEQ ID NO:2:

```
CTGGAAAAAA ACTTAAGTGT TCAGCAACAA GAGAATGGAT ACATAAATAA TGATCTATTC      60

CCAAAATTGA TTTTTTTTTT TGAGACAGGG TCTTGCTCTG TTGCCCAGGC TAGAGTGCAG     120

TGGCATGATC ATGGCTCACT GCAGTCTCAA CCTCCTGGGC TCAAGCAATC CTCCTACCTC     180

AGCCTCCTGA GTAGCTGAGA CCACAGGCAC AACCCATCAC ACCCAGCTAA TTTTATTTTT     240

TTTGTAGAGA TGGGGTCTC ACTATGTTGC CCAGGCTGGT CTTGAACTCC TGGGCTCAAA      300

TGATCCACCC ACCTCGGCCT CCAAAGTGCT GGGATAATAC CTCCCCAGCC GGATATTTTA     360

AAGCAGTGAA AATGAATGGT CTACACATAG CCACATGAAT GAATCTTATT AATACATTAA     420

GTGAAAAAAA GCAAAGGTCA CAGAGGAATA CATACATTTT AATACCATTT ATATAAAGCT     480

CAAAATATGT GAAATACCAC TATCTATTGT TTAGGGATAT ATACATAAGT AGTGTAAGTA     540

TACAGAAATA TAAGGAAATG AAAAATATCA AATCTTCATT TTCATCTGAA GTGGTTACTT     600

CAGGGGCTGT GGCAGGGAGA GAGAGATGCA GCTGAGGAAG AGTCCATAGG GGGCTTCAAC     660

TATATTAGCA ATATTGTATT TCTTATGCTT GGTGGTGGGG ATAGGTATGT TTGAAATGTA     720

ATCCTTTAAG CATGAAATAA CTCTTCAAAA ATGAAATATT TCAGGCTGTG CACAGTGGCT     780

CAGGCATTGT AATCCCAGCA TGTTGGGAGG CTGAACGTGG GCGGATCACC GTGAGGTCAG     840

GAGTTTGAGA CCAACCTGGC CAACATGGTG AAATCCCATC TCTACTAAAA ATACAAAAAT     900

TAGCCAGGTG TGGTGGCAGG TGACTGTAAT CCCAGCTACT GGGAGGCTG AGGCAGGAGA      960

ATCGCTTGAA TCTGGGAGGT GGAGGTTGCA GTGAGCCGAG ATCACGCCAC TGCATTACAG    1020

CAAGACTCCA TCTCAAAAAA AGAAAAAAA AAAAGAAAAA AGAAATGTTT CATAATTTTT     1080

AATAAAAGGC AAGACAATAT AAATTGGTAG TTATTTAAGT CATTCTACTT TTCCTGAGGC    1140

CCAGTGCAGG AAAACAAAGT TCCTATCCTT GTTCCAACTA GACCATTTTG ATAAGCTGCA    1200

AAAAGAAAAG ACTTTGATGC TATTTCTTAG CCAGTTTGCA ACAGCTGAGA GGTGAGCATG    1260

GAAGCTCTTG CATATATTCA GTTCAGAGAA TGGGTGCTTA GTTTATGTCC AGAGTTTGTC    1320

CCAGATTTCA CTATGACGTC AGCTCTCCGG GGAGAAGTAT ATAAAATAAA AGTTAAAAT     1380

CCCTCTCAGT CCTTTACCCA ATCCTATTCC CCAGAGGTAA TCTCTATTGA CAGTACCCCT    1440

CCAGATATTT TCCCTATGTA TATACAAATA CACAGATACA CACTGAAAGT TAATTTTGGC    1500

CAGGTGCAGT GGCTCCTGCC TATACCAGAG GATTGCTTGA GTGCAGGAGT TCAAGACCAG    1560

CCTGGGCAAC ATAGCGAGAC CACATCTCTA GTAAAAATAA AAAAAAATAG CTAGGCGTGG    1620

TGGCACAGTG GCACGTACCT TTAGTCTCAG CTACTCGGGT GGTTGAGGTG GAGAATCACT    1680

TGAGCCCGGG GAGGTCAAGC CTACAATTAG CTGTGATTGC TTCACTGCAC TATAGCCTGG    1740

GCAACAGAGC TAGACCCTGT CTCAAAAAAA TAATAATAAA TTTTATATAT ATATATGAGG    1800

ATGAAATTAC ATATGTATTA TTTGAACAGA AGTGAAATCT TTTCTTTTTT TTTTTCAGAC    1860

AGAATCTTGC CGCATGACCC AGGCTAGAAT GCAGTGGTGT GATCTCGGCC CTCTGCAACC    1920

TCCACCTCCC AGGTTCAAGC GATTCTCATG CCTCGGTCTC CCAAGTAGCT GGGATTACAG    1980
```

-continued

```
GCATGCACCA CCATGCCCAG CTAATTTTTG TATTTTTCGT AGAGACGTTC GCCATATTGG      2040

CCAGGCTGGT CTCAAACTCC TGGCCTCAAG TGATCTGCCC ACCTCGGCCT CCCAAAGTGC      2100

CAGCAGCATG CTCGGAGGAG TGACTTTAAA GCTTTTCTAC TTGCTTCCTA GAGTAAGGGA      2160

CGCATTTTAC ACTGCTATCC AAAACTCATC ATAGAAACAT ACACACACAA AACCAAAGCA      2220

CACATATACA ACTGAGCAAA TATTTCATGA CATAACACTT TCTCTTACTA AGGGTGACGC      2280

GCTGAAATTT TGTATTCTGT CCTATTTCAT TTTTTAAAAA TGGTAACCAT GACCTGCTAA      2340

ATTGATTTCA TTGTCCACTA ATAAATTATG ACCTCAGTTT CAAAAAGATT GCTTTAGGTA      2400

ACCAATCATC TTCTGAGATT TATACAGATT GCTCATAATT CTCTCCTATT TTTTAAAAAC      2460

ATGCTGCAGT GAACTGCTTT ACACTCATTT TATGACTACT TCTGAGACCA AGATCCCGGA      2520

TTATGTAATT GTTATTTACT TAAAATTCTG GTAAAATGTA GCCATTATAC TGGAAAACTA      2580

AATTTTAATC TTGGATCTGT CACCACCATG ATATATAAAC TTTGGGCAAG TCCCTGCACC      2640

TCTCTGGACC TCAATCTCCC CATCAGCAAC CTGCTGATCC TACTCCCAGG AGTGTGCTCT      2700

AAGTTGAAAG TAGATGCCCC ACCCCCTGAG TCAGCGCCGG CAGGACTTCT CACCAAGCCC      2760

TTCTCCCCCT TTTCCGCTCC CTGTTCCTGG TTCCTAGGAA GCAGCCCAAG GAGAAGGGAA      2820

AAGGCAGGTC TGGGCAGGAG GGAGCAATGA AGGGCGGGGC AGAGGGAGGG CAGGAGGGAG      2880

GCCGGCCCCC TAGTAGGAAA TGAGACACAG TAGAAATAAC ACTTTATAAG CCTCTTCCTC      2940

CTCCCATCTC CTGGCCTCCT TCCATCCTCC TCTGCCCAGA CTCCGCCCCT CCCAGACGGT      3000

CCTCACTTCT CTTTTCCCTA GACTGCAGCC AGCGGAGCCC GCAGCCGGCC CGAGCCAGGA      3060

ACCCAGGTCC GGAGCCTCAA CTTCAGGATG TTGACAACAT TGCTGCCGAT ACTGCTGCTG      3120

TCTGGCTGGG CCTTTTGTAG CCAAGACGCC TCAGATGGTG AGTCGGGGGC ACATCTCCTG      3180

CCTCAGGATG GTTCTGGAGA ATCTCAGTCT ATCTGGGCAC ATGG                      3224
```

(2) INFORMATION FOR SEQ ID NO:3:

(i) SEQUENCE CHARACTERISTICS:
        (A) LENGTH: 8 base pairs
        (B) TYPE: nucleic acid
        (C) STRANDEDNESS: single
        (D) TOPOLOGY: linear    (ii) MOLECULE TYPE: DNA (genomic)

(iii) HYPOTHETICAL: NO

(iv) ANTI-SENSE: NO

(xi) SEQUENCE DESCRIPTION: SEQ ID NO:3:

```
CCCACCCC                                                                 8
```